US009645412B2

(12) United States Patent
Wildsmith et al.

(10) Patent No.: US 9,645,412 B2
(45) Date of Patent: May 9, 2017

(54) CUSTOMIZED LENS DEVICE AND METHOD

(71) Applicant: Johnson & Johnson Vision Care, Inc., Jacksonville, FL (US)

(72) Inventors: Christopher Wildsmith, Jacksonville, FL (US); Michael F Widman, Jacksonville, FL (US)

(73) Assignee: Johnson & Johnson Vision Care Inc., Jacksonville, FL (US)

( * ) Notice: Subject to any disclaimer, the term of this patent is extended or adjusted under 35 U.S.C. 154(b) by 80 days.

(21) Appl. No.: 14/534,106

(22) Filed: Nov. 5, 2014

(65) Prior Publication Data

US 2016/0124245 A1   May 5, 2016

(51) Int. Cl.
| | |
|---|---|
| *A61B 3/02* | (2006.01) |
| *G02C 7/02* | (2006.01) |
| *G02C 7/04* | (2006.01) |
| *A61B 3/028* | (2006.01) |
| *A61B 3/103* | (2006.01) |
| *A61B 3/10* | (2006.01) |

(52) U.S. Cl.
CPC ............ *G02C 7/027* (2013.01); *A61B 3/0285* (2013.01); *A61B 3/103* (2013.01); *A61B 3/1015* (2013.01); *G02C 7/047* (2013.01)

(58) Field of Classification Search
CPC ......... A61B 3/0285; A61B 3/036; A61B 3/04; A61B 3/1015; A61B 3/103; A61B 3/1035; G02C 7/027; G02C 7/047; G02C 7/049
USPC ...... 351/159.74, 159.77, 205, 222, 223, 246
See application file for complete search history.

(56) References Cited

U.S. PATENT DOCUMENTS 3,658,528 A   4/1972 Berman
3,916,033 A   10/1975 Merrill
(Continued)

FOREIGN PATENT DOCUMENTS

CN   101017208 A   8/2007
EP      207640 A2   1/1987
(Continued)

OTHER PUBLICATIONS

Cabral, J.T., et al; Propagating waves of network formation induced by light, Polymer 46 (2005) pp. 4230-4241.
(Continued)

*Primary Examiner* — Huy K Mai

(57) ABSTRACT

A system and method for identifying a custom contact lens for a patient. The method includes receiving as input results from a bare eye examination of a patient including at least a measured sphere power; receiving as input a target or actual measured sphere power of a selected fitting lens; receiving as input results of an over-refraction examination of a patient wearing the fitting lens, wherein the results of the over-refraction examination include at least a measured sphere power; calculating the power delivered by the fitting lens on the patient's eye based on input received from the bare eye examination and over-refraction examinations; calculating an Effectiveness Ratio using the calculated power delivered by the fitting lens and the target or actual measured sphere power of the fitting lens; and calculating a custom lens power for the patient using the Effectiveness Ratio and measured sphere power from the bare eye examination.

34 Claims, 2 Drawing Sheets

(56) References Cited

U.S. PATENT DOCUMENTS

| | | | |
|---|---|---|---|
| 4,701,288 A | 10/1987 | Cook | |
| 4,702,574 A | 10/1987 | Bawa | |
| 4,943,150 A | 7/1990 | Deichert et al. | |
| 4,988,274 A | 1/1991 | Kenmochi | |
| 5,114,628 A | 5/1992 | Hofer | |
| 5,166,710 A | 11/1992 | Hofer | |
| 5,182,056 A | 1/1993 | Spence | |
| 5,200,121 A | 4/1993 | Hagmann | |
| 5,219,497 A | 6/1993 | Blum | |
| 5,229,797 A | 7/1993 | Futhey et al. | |
| 5,396,045 A | 3/1995 | Opdyke | |
| 5,452,031 A | 9/1995 | Ducharme | |
| 5,462,700 A | 10/1995 | Beeson | |
| 5,502,518 A | 3/1996 | Lieberman | |
| 5,517,260 A | 5/1996 | Glady | |
| 5,650,837 A | 7/1997 | Roffman | |
| 5,662,706 A | 9/1997 | Legerton | |
| 5,685,420 A | 11/1997 | Martin | |
| 5,730,911 A | 3/1998 | Cano | |
| 5,782,460 A | 7/1998 | Kretzschmar et al. | |
| 5,983,201 A | 11/1999 | Fay | |
| 6,086,204 A | 7/2000 | Magnante | |
| 6,142,628 A | 11/2000 | Saigo | |
| 6,145,988 A | 11/2000 | Manfredini | |
| 6,200,646 B1 | 3/2001 | Neckers | |
| 6,233,102 B1 | 5/2001 | Hogan, Jr. | |
| 6,241,355 B1 | 6/2001 | Barsky | |
| 6,305,802 B1 | 10/2001 | Roffman | |
| 6,340,229 B1 | 1/2002 | Lieberman | |
| 6,413,251 B1 | 7/2002 | Williams | |
| 6,457,826 B1 | 10/2002 | Lett | |
| 6,471,891 B1 | 10/2002 | Cameron | |
| 6,499,843 B1 | 12/2002 | Cox | |
| 6,520,958 B1 | 2/2003 | Shimmick | |
| 6,595,639 B1 | 7/2003 | Ho | |
| 6,598,975 B2 | 7/2003 | Liang | |
| 6,616,275 B1 | 9/2003 | Dick | |
| 6,626,534 B1 | 9/2003 | DiMartino | |
| 6,800,225 B1 | 10/2004 | Hagmann et al. | |
| 6,827,885 B2 | 12/2004 | Altmann et al. | |
| 6,842,223 B2 | 1/2005 | Tyminski | |
| 6,935,743 B2 | 8/2005 | Shadduck | |
| 6,966,649 B2 | 11/2005 | Shadduck | |
| 6,997,428 B1 | 2/2006 | Andino et al. | |
| 7,029,119 B2 | 4/2006 | Youssefi | |
| 7,128,866 B1 | 10/2006 | Henningsen | |
| 7,172,285 B1 | 2/2007 | Altmann | |
| 7,235,195 B2 | 6/2007 | Andino et al. | |
| 7,293,871 B2 | 11/2007 | Dreher | |
| 7,350,920 B2 | 4/2008 | Levine | |
| 7,384,146 B2 | 6/2008 | Covannon | |
| 7,860,594 B2 | 12/2010 | Andino et al. | |
| 7,905,594 B2 | 3/2011 | Widman | |
| 2001/0047217 A1 | 11/2001 | Buazza et al. | |
| 2002/0024631 A1 | 2/2002 | Roffman | |
| 2002/0071094 A1 | 6/2002 | Roffman | |
| 2002/0071097 A1 | 6/2002 | Ross | |
| 2002/0140902 A1 | 10/2002 | Guirao | |
| 2002/0154271 A1 | 10/2002 | Donitzky | |
| 2003/0003295 A1 | 1/2003 | Dreher | |
| 2003/0007123 A1 | 1/2003 | Broderick | |
| 2003/0030161 A1 | 2/2003 | Pegram | |
| 2003/0053031 A1 | 3/2003 | Wirth | |
| 2003/0117580 A1 | 6/2003 | Franz | |
| 2003/0128336 A1 | 7/2003 | Jethmalani | |
| 2004/0004287 A1 | 1/2004 | Shimizu et al. | |
| 2004/0015261 A1 | 1/2004 | Hofmann | |
| 2004/0041287 A1 | 3/2004 | Engardio | |
| 2004/0046287 A1 | 3/2004 | Andino | |
| 2004/0046931 A1 | 3/2004 | Legerton | |
| 2004/0054358 A1 | 3/2004 | Cox | |
| 2004/0064376 A1 | 4/2004 | Yoshida | |
| 2004/0100619 A1 | 5/2004 | Olivier | |
| 2004/0119174 A1 | 6/2004 | Hofmann | |
| 2004/0169820 A1 | 9/2004 | Dai | |
| 2004/0169932 A1 | 9/2004 | Esch | |
| 2004/0179167 A1 | 9/2004 | Dahi | |
| 2004/0215525 A1 | 10/2004 | Keane | |
| 2004/0222539 A1 | 11/2004 | Hagmann | |
| 2004/0233382 A1 | 11/2004 | Lindacher | |
| 2004/0246440 A1 | 12/2004 | Andino | |
| 2004/0263779 A1 | 12/2004 | Schroder | |
| 2004/0263785 A1 | 12/2004 | Chernyak | |
| 2004/0263786 A1 * | 12/2004 | Williams | A61B 3/0025 351/246 |
| 2005/0041203 A1 | 2/2005 | Lindacher | |
| 2005/0056954 A1 | 3/2005 | Devlin | |
| 2005/0060196 A1 | 3/2005 | Tsushi | |
| 2005/0068489 A1 | 3/2005 | Hall | |
| 2005/0073648 A1 | 4/2005 | Toshima | |
| 2005/0074616 A1 | 4/2005 | Harchanko | |
| 2005/0089670 A1 | 4/2005 | Large | |
| 2005/0090612 A1 | 4/2005 | Soane | |
| 2005/0098478 A1 | 5/2005 | Gupta | |
| 2005/0099595 A1 | 5/2005 | Lindacher | |
| 2005/0105044 A1 | 5/2005 | Warden | |
| 2005/0105045 A1 | 5/2005 | Legerton | |
| 2005/0105048 A1 | 5/2005 | Warden | |
| 2005/0122472 A1 | 6/2005 | Fisher | |
| 2005/0131398 A1 | 6/2005 | Campbell | |
| 2005/0219461 A1 | 10/2005 | Hirohara | |
| 2005/0259221 A1 | 11/2005 | Marmo | |
| 2005/0264756 A1 | 12/2005 | Esch | |
| 2005/0275137 A1 | 12/2005 | Stolpe | |
| 2006/0001184 A1 | 1/2006 | Phelan | |
| 2006/0055071 A1 | 3/2006 | Kendig | |
| 2006/0055884 A1 | 3/2006 | Molinari | |
| 2006/0100408 A1 | 5/2006 | Powell et al. | |
| 2006/0173644 A1 | 8/2006 | Dai | |
| 2006/0192310 A1 | 8/2006 | Lindacher | |
| 2006/0192919 A1 | 8/2006 | Lindacher | |
| 2006/0232743 A1 | 10/2006 | Legerton | |
| 2006/0256451 A1 | 11/2006 | Schaack | |
| 2006/0264917 A1 | 11/2006 | Tuan | |
| 2006/0268225 A1 | 11/2006 | Lieberman | |
| 2006/0279696 A1 | 12/2006 | Perez | |
| 2007/0023942 A1 | 2/2007 | Andino | |
| 2007/0038202 A1 | 2/2007 | Celestino | |
| 2007/0091259 A1 | 4/2007 | Svochak | |
| 2007/0097318 A1 | 5/2007 | Chehab | |
| 2007/0103639 A1 | 5/2007 | Nellissen et al. | |
| 2007/0109497 A1 | 5/2007 | Chang | |
| 2007/0132949 A1 | 6/2007 | Phelan | |
| 2007/0273828 A1 | 11/2007 | Polland | |
| 2007/0274626 A1 | 11/2007 | Sabeta | |
| 2007/0284770 A1 | 12/2007 | Ansell | |
| 2007/0285760 A1 | 12/2007 | Ho | |
| 2008/0013043 A1 | 1/2008 | Ye | |
| 2008/0017977 A1 | 1/2008 | Tseng | |
| 2008/0043200 A1 | 2/2008 | Ishak | |
| 2008/0055545 A1 | 3/2008 | Clamp | |
| 2008/0067702 A1 | 3/2008 | Yao | |
| 2008/0079184 A1 | 4/2008 | Yin | |
| 2008/0079895 A1 | 4/2008 | Jubin | |
| 2008/0137030 A1 | 6/2008 | Hoffman | |
| 2008/0143003 A1 | 6/2008 | Phelan | |
| 2008/0143004 A1 | 6/2008 | De Wilt | |
| 2008/0143960 A1 | 6/2008 | MacRae | |
| 2008/0143963 A1 | 6/2008 | Lindacher | |
| 2008/0165324 A1 | 7/2008 | Lindacher | |
| 2008/0179770 A1 | 7/2008 | Rooney | |
| 2008/0192201 A1 | 8/2008 | Wengler | |
| 2008/0277811 A1 | 11/2008 | Miller | |
| 2008/0288369 A1 | 11/2008 | Hunter | |
| 2008/0291395 A1 | 11/2008 | Dai | |
| 2008/0306573 A1 | 12/2008 | Campin | |
| 2008/0309873 A1 | 12/2008 | Levecq | |
| 2009/0022274 A1 | 1/2009 | Gertner | |
| 2009/0033920 A1 | 2/2009 | Simpson | |
| 2009/0051059 A1 | 2/2009 | Widman | |
| 2009/0174863 A1 | 7/2009 | Widman | |

(56) References Cited

U.S. PATENT DOCUMENTS

| | | | |
|---|---|---|---|
| 2010/0230837 A1 | 9/2010 | Zanini et al. | |
| 2014/0002799 A1* | 1/2014 | Wildsmith | A61B 3/00 351/223 |
| 2015/0077704 A1* | 3/2015 | Carmon | A61B 3/028 351/159.74 |

FOREIGN PATENT DOCUMENTS

| | | |
|---|---|---|
| EP | 322353 | 6/1989 |
| EP | 0637471 | 2/1995 |
| EP | 637491 B1 | 11/1997 |
| EP | 1750162 A2 | 2/2007 |
| EP | 1818692 A2 | 8/2007 |
| EP | 1552336 B1 | 10/2008 |
| EP | 2679146 | 1/2014 |
| GB | 1449685 A | 9/1976 |
| JP | 01-198312 | 9/1989 |
| JP | 1-198312 | 9/1998 |
| JP | 2001290978 A | 10/2001 |
| JP | 2002078681 A | 3/2002 |
| JP | 2002357796 A | 12/2002 |
| JP | 2003295134 A | 10/2003 |
| RU | 2116891 C1 | 8/1998 |
| WO | WO 9300816 | 1/1993 |
| WO | WO 9308016 | 4/1993 |
| WO | WO 9729441 A1 | 8/1997 |
| WO | WO 9733742 A1 | 9/1997 |
| WO | WO 9842497 A2 | 10/1998 |
| WO | WO 9842497 A3 | 10/1998 |
| WO | WO 0102881 | 1/2001 |
| WO | WO 0221753 | 3/2002 |
| WO | WO 0233628 A2 | 4/2002 |
| WO | WO 03013832 | 2/2003 |
| WO | WO 03037716 A2 | 5/2003 |
| WO | WO 03077792 | 9/2003 |
| WO | WO 2004022318 A2 | 3/2004 |
| WO | WO 2004034095 | 4/2004 |
| WO | WO 2004039554 A2 | 5/2004 |
| WO | WO 2004022318 A3 | 6/2004 |
| WO | WO 2005005121 A2 | 1/2005 |
| WO | WO 2005005121 A3 | 1/2005 |
| WO | WO 2005007386 A2 | 1/2005 |
| WO | WO 2005007386 A3 | 1/2005 |
| WO | WO 2005098478 A1 | 10/2005 |
| WO | WO 2006010632 A1 | 2/2006 |
| WO | WO 2006034864 A1 | 4/2006 |
| WO | WO 2009025848 A2 | 2/2009 |

OTHER PUBLICATIONS

European Search Report EP 13 15 9083 Date of Completion Oct. 22, 2013.

* cited by examiner

CUSTOMIZED LENS DEVICE AND METHOD

FIELD OF THE INVENTION

The present invention relates generally to the field of contact lenses, and more particularly to a system and method for providing customized contact lenses for patients.

BACKGROUND

The use of contact lenses to correct vision is common place in today's world. There are presently several traditional methods of high-volume low-cost contact lens manufacture. These methods include, but are not limited to, cast molding, spin casting, lathing, and using a technique known in the industry as "Lightstream Technology", and any combinations thereof.

Traditional cast molding involves the use of diamond point turning technologies to produce metal tools (also referred to as inserts) that are used in the injection molding process to produce male and female plastic lens molds. Liquid monomer is then placed between the pair of male/female molds and is then cured. Subsequently, the cured lens is removed from the mold pair and undergoes post processing steps (including hydration, release, sterilization, inspection, measurement, packaging, etc.) which results in a usable product.

Typically, spin casting also involves the use of diamond point turning technologies to produce metal tools that are used in the injection molding process to produce female plastic lens molds, into which liquid monomer is dosed. The mold and monomer are then spun about a central axis while being exposed to curing radiation and the lens is formed. Similar to cast molding, the cured lens is removed from the lens mold and undergoes post processing steps (including hydration, release, sterilization, inspection, measurement, packaging, etc.) which results in a usable product. Due to the fact that the concave surface of the lens is easily accessible when created by spin casting, this surface and lens thicknesses can be measured pre-hydration if desired.

Typically, lathing involves the use of diamond point turning technologies to produce pre-hydrated lenses directly from lens blanks (also called buttons). The pre-hydrated lens then undergoes post processing steps including hydration, sterilization, inspection, measurement, packaging, etc., which results in a usable product. Due to the fact that both surfaces of the pre-hydrated lens are easily accessible when created by diamond point turning of buttons, the pre-hydrated lens can be more fully measured in its pre-hydration state if desired.

Diamond point turning can also be used to produce the lens molds directly, with these lens molds being utilized in the cast molding or spin casting descriptions above.

"Lightstream Technology" is a technology used by Ciba Vision Corporation of Duluth, Ga. (now Alcon) which involves the use of re-usable glass mold pairs instead of plastic molds. Each glass mold pair consists of a concave surface mold and a convex surface mold that are submerged in lens monomer, placed close to each other so that the gap between the two curved surfaces map to the desired pre-hydrated contact lens profile. The monomer is cured through the glass molds using ultraviolet light, the molds separated and then the lens undergoes stages including hydration, sterilization, inspection, measurement, packaging, etc., which results in a usable product.

Most contact lenses produced and sold today are in discrete parameter ranges, which include limited base curves, diameters and powers. Sphere power offerings vary by manufacturer, but are usually in the range of $-20.00$ D to $+20.00$ D, more likely $-12.00$ D to $+8.00$ D. Typically, powers within these ranges are only offered in 0.25 D steps (between the range of $-6.00$ D and $+6.00$ D powers) and 0.50 D steps outside the $\pm 6.00$ D range. Currently, most cylinder power offerings are also in discrete steps, with each manufacturer having their own ranges. The Acuvue® brand of astigmatic lenses, manufactured and sold by Johnson & Johnson Vision Care of Jacksonville, Fla., for example, currently only offers $-0.75$ D, $-1.25$ D, $-1.75$ D and $-2.25$ D of cylinder correction. The available power axes of astigmatic lenses are also limited, typically in 10° steps, ranging from 0° to 180° for low cylinder powers, and restricted by some manufacturers further to say 80°, 90°, 100°, 170°, 180° and 190° (the 180° and 190° angles may be referred to as the 0° and 10° angles respectively) offerings for high cylinder powers.

The reasons for manufacturers only offering discrete steps in contact lens parameters are many fold, but may include the cost of tool and mold manufacture, inventory costs for storing large numbers of stock keeping units (SKUs) of the tools, inventory costs of storing huge quantities of lenses, the low prevalence of patients needing higher degrees of power correction, etc. As an example, consider the number of SKUs for a fictional astigmatic product called "BrandX" which has 1 base curve offering and 1 diameter offering. A sphere power range of $-6.00$ D to $+6.00$ D in 0.25 D steps for BrandX results in 49 different SKUs. Cylinder power offerings of say $-0.75$ D, $-1.25$ D, $-1.75$ D and $-2.25$ D along just one axis quadruples the number of SKUs to 196. Axis offerings for BrandX, say at every 10° for each of the cylinder powers, multiplies the SKUs by 18 to give 3528 SKUs. Each incremental cylinder power offering at each of the 10° axes adds 882 SKUs to BrandX's portfolio. If cylinder powers were offered in 0.25 D steps from $-0.25$ D to $-2.25$ D, the total number of BrandX SKUs would be 7938. Just one additional base curve offering doubles the SKUs to 15,876, and adding just one other diameter to the mix doubles the total again to 31,752 SKUs. Offering BrandX's axes in 5° instead of 10° increments also doubles the number of SKUs to 63,504. Offering BrandX in alternate materials also drastically increases the number of SKUs.

Offerings of different lens designs, power, base curve, diameter and shape all require different tools to be made. In a cost range of $100-$500 per metal tool, cast molding for a large number of SKUs is a very expensive proposition, especially when multi-cavity technology is used wherein multiple tools of the same design are used in each mold block. Manufacturers therefore are selective as to the number of different contact lens design options they produce, which typically are chosen to align with the most commonly prevalent vision need/ordered prescriptions. This, of course, means that individuals whose prescriptions fall between or outside those ranges offered by manufacturers must purchase lenses that are less than optimal in correcting their particular vision or fit needs.

With traditional manufacturing techniques, once the mold has been established for a given prescription, each product manufactured from that mold is labeled with that given target prescription, including power, and the lenses themselves are not further measured individually. In other words, the lenses produced are labeled with the target prescription and not labeled with respect to the actual parameters of the resulting product. Measurements are not performed on each manufactured lens since to do so each lens must be removed from the mold, hydrated, restrained and separately held.

Performing these stages and precisely measuring each lens is time consuming, difficult, and expensive enough so as to be prohibitive.

In reality, high volume low cost hydrogel contact lens manufacture results in variations within each lot of lenses, and between lots. The ANSI Standard Z80.20 and BS EN ISO 18369-2:2012 standard defines as acceptable a back vertex power tolerance of ±0.25 D for the sphere power range of −10.00 D to +10.00 D, a ±0.50 D tolerance for sphere powers in the ranges of −20.00 D to −10.01 D and +10.01 D to +20.00 D, and a ±1.00 D tolerance beyond −20.00 D and beyond +20.00 D. Both standards also show tolerances on cylinder power of ±0.25 D for cylinder powers up to and including −2.00 D, a ±0.37 D tolerance for cylinder powers between the range of −2.01 D to −4.00 D, and a ±0.50 D tolerance for cylinder powers beyond −4.00 D. Manufacturers typically monitor lens parameters on a sampling basis to ensure that parameters are within upper and lower specification limits. If the mean of any measured parameter drifts too far from the desired target, manufacturers can adjust a multitude of process parameters to re-center the mean. Variations in power of high volume low cost lenses may result from many sources, which when combined with metrology inaccuracies can typically result in a ±0.15 D deviation from target, but can be anywhere within the limits described above. In summary, the actual lens power of any commercially available high-volume low-cost lens is not known exactly, as only the labeled (targeted) lens power is available for reference.

More recently, a new system and method for manufacturing contact lenses has been disclosed in which an infinite number of different lens shapes and lens parameters (including lens powers) can be produced on a custom basis. U.S. Pat. No. 8,317,505, which is incorporated herein by reference in its entirety, discloses a method for growing a Lens Precursor Form on a single male optical mandrel on a voxel by voxel basis by selectively projecting actinic radiation through the optic mandrel and into a vat or bath of liquid polymer. The optical mandrel and Lens Precursor Form are then removed from the vat and inverted so that the convex surface of the optic mandrel is upright. Following a dwell period during which uncured residual liquid monomer from the bath that remains on the Lens Precursor Form flows under gravity over the Lens Precursor Form, such liquid is then cured to form the final lens. As described therein, a custom lens can be produced for any given eye.

For customized lenses manufactured as set forth in U.S. Pat. No. 8,317,505, it is possible to measure the power of each lens as it is produced (in its pre-hydrated state and converting the values through known calibration parameters to a precise wet lens measurement, or measuring the wet powers of each completed lens after hydration) rather than relying on targeted lens power. As the formed lens is held in place on the male mandrel, precise measurements of the pre-hydrated lens can quickly and easily be performed by using any known capable technique. Examples of suitable measurement techniques include but are not limited to wavefront measurements and non-contact thickness profile measurements. Wavefront measurements may be employed in a manner and via the use of equipment such as that described in U.S. Patent Publication No. 2012/0133957, which is incorporated herein by reference in its entirety. Data from wavefront metrology can easily be transferred into aberration profile data, including sphere, cylinder and axis. Alternatively, lens thickness information may be gathered by the use of, for example, non-contact opto-mechanical profilometry. There are many pieces of equipment capable of taking these measurements, one example would be a system where a Keyence non-contact probe (Keyence Corporation of America, Itasca, Ill.) is mounted on an air bearing rotation stage, with the optic mandrel being mounted on another air bearing rotation stage and the motion of both the part to be measured and the probe are synchronized and coordinated as to map the desired surface are of the part under consideration. Data from non-contact opto-mechanical profilometry can easily be transferred into aberration profile data, including sphere, cylinder and axis. Other suitable measurement techniques and devices may also be used.

The ability to manufacture and readily measure a custom lens creates new opportunities for the eye care practitioner to be able to dispense more accurate contact lenses to their patients. For this to effectively occur, however, the eye care practitioner (ECP) must be able to identify a more precise prescription for the patient.

In a typical setting, a patient's vision will be evaluated by any known means, and an initial desired lens power will be identified. A fitting or trial lens having close to the desired power will be placed on the patient's eye, and depending on how the patient sees with that given lens, the lens power may be adjusted up or down, which with traditional lenses is limited by the commercially available 0.25 diopter steps in lens sphere power and the limited available cylindrical powers as detailed above. For traditional lenses where only label (target) power is known as opposed to the actual measured lens power of the first fitted lens or any subsequently selected lens, the process is sub-optimal. Further, the subjective refraction and over-refraction exams are typically low resolution, limited to 0.25 D increments. Consider a patient with an actual spherical power need of −2.875 D. Using course 0.25 D resolution phoropters, this vision requirement will only be measured as either −2.75 D or −3.00 D to the nearest 0.25 D increment. Assume the ECP uses the −2.75 D value as the patient's perceived need, a first fitting lens labeled as −2.75 D may be selected and placed on the eye. This lens though could actually measure anywhere from −2.50 D to −3.00 D, as per the ANSI standard. If the over-refraction exam returns a value of −0.25 D, the ECP may select another fitting lens labeled −3.00 D and repeat the exam, or order −3.00 D lenses for the patient. The delivered lenses could range from −2.75 D to −3.25 D (as per the ISO standards) but yet the patient's true need was −2.875 D, yielding sub-optimal vision correction. Consider the case where the actual sphere power of the initial fitting lens labeled as a −2.75 D was really a −3.00 D lens, then based off the −0.25 D over-refraction the lens the patient really needs would be a −3.25 D indicating that the delivered lenses to the patient could be 0.375 D away from optimal correction. This situation using a coarse refraction, unknown actual fitting lens powers and course over-refraction exams leading to sub-optimal vision applies equally to the use of astigmatic fitting lenses; commercial products used as fitting or trial lenses, and intended correction of astigmatic, multifocal, higher order aberrated and diseased eyes.

As described further below, while it is preferable that the exact powers of the fitting lenses be known, and for high resolution exams to be performed in order to obtain the best results, the system and methods of the present invention will nevertheless provide a more precise prescription for a patient regardless of whether currently available stock lenses and low resolution exams are used.

Phoropters, refractometers or aberrometers, manual or automated, are frequently used in the ECP office to determine a patient's vision requirement via refraction exams or over-refraction exams. "Refraction exams" are typically conducted through the patient's bare eye (that is when vision correction is not worn) and often referred to as "bare eye exams". "Over-refraction exams" are performed when the patient is wearing vision correction (typically contact lenses). Both phoropters and refractometers have the capability of outputting a sphere power component, a cylinder power component and an axis component.

Glass lenses of different power are typically embedded in auto-phoropters, whereas manual phoropters basically consist of a trial frame into which ECPs can manually place supplemental glass lenses of different power. In both manual and auto-phoropters, these glass lenses are placed in the line-of-sight of the patient as he/she looks through the unit towards a vision target. While looking through the unit, the ECP selects appropriate glass lenses of different power and asks the patient which one is "better or worse". The ECP does this to refine his/her patient's prescription. Exams performed using phoropters are typically referred to as "subjective exams" since the patient gives their opinion on which lenses are "better or worse" for them.

Typically ECPs use both manual and auto-phoropters in 0.25 D power increments although some have the capability of using 0.125 D steps, and 5° axis increments. Refractometers and aberrometers typically display power data to the nearest one hundredth of a diopter, and the nearest whole integer for axis in degrees. Exams performed using refractometers and aberrometers are typically referred to as "objective exams" since the equipment just returns numerical and graphical values, with little to no patient involvement in the decision making process. One example of an auto-refractometer is the Nidek ARK-10000 Refractive Power/Corneal Analyzer (Nidek Inc. of Freemont, Calif.). The 0.01 D power resolution and 1° axis resolution of refractometers and aberrometers suggests that they would be ideal for use in the process of prescribing custom lenses, however, objective exams performed on currently available equipment do not take into account how the brain perceives and analyzes the images presented to it by the ocular system and therefore do not always provide the best prescriptive data for all patients. When fitted with lenses prescribed via the use of subjective data compared to lenses prescribed off objective data, some patients prefer the "subjective lenses" and others prefer the "objective lenses". This being said, the sphere, cylinder and axis data from objective exams can be used alone, or in combination with data from subjective exams to provide the best possible custom lens design for the patient.

As will be described further below, data from at least two eye exams are required for the present invention, a bare eye exam and an over-refraction exam. The exams do not need to be concurrent, but it is preferable if they are since day to day variations in eye performance can affect the results. It is also preferable, but not essential, to perform the exams using the same equipment since any differences in calibration and performance between similar but different units may also affect the results. Subjective or objective exams may be used for both the refraction and over-refraction exams, or any combination thereof.

In summary, the invention described herein will work with high resolution data, low resolution data or a combination of high and low resolution data; with data from subjective exams, objective exams or a combination of both subjective and objective exams; or with a new breed of objective equipment that purports to support subjective responses. The methods highlighted will further work with any pertinent value of sphere power, cylinder power and axis information extracted from any measurement equipment and technique, including phoropters, refractometers and aberrometers. Further, the invention described herein is applicable to all types of required vision correction needs, including single vision, multifocal vision, astigmatic vision, higher order aberration correction needs as well as diseased eyes, such as Keratoconus.

SUMMARY OF THE INVENTION

The present invention provides a method for identifying a custom contact lens for a patient, including the steps of receiving as input results from a bare eye examination of a patient including at least a measured sphere power; receiving as input a target or actual measured sphere power of a selected fitting lens; receiving as input results of an over-refraction examination of a patient wearing said fitting lens, wherein the results of the over-refraction examination include at least a measured sphere power; calculating the power delivered by the fitting lens on the patient's eye based on input received from the bare eye examination and over-refraction examinations; calculating an Effectiveness Ratio using the calculated power delivered by the fitting lens and the target or actual measured sphere power of the fitting lens; and calculating a custom lens power for the patient using the Effectiveness Ratio and measured sphere power from the bare eye examination.

In alternate embodiments, either the actual measured sphere power of the fitting lens is received as input and the Effectiveness Ratio is calculated using the actual measured sphere power, or the target lens sphere power of the fitting lens is received as input and the Effectiveness Ratio is calculated using the target lens sphere power.

The bare eye examination may be a subjective examination, and may be performed using a phoropter. In an alternative embodiment, the bare eye examination may be an objective examination and may be performed using a refractometer or a device that measures the wavefront of the patient's eye. In yet another embodiment, the bare eye examination may be a combination subjective and objective examination.

According to yet another embodiment, the method further includes the step of generating a custom contact lens prescription for the patient based on the calculated custom lens power. In alternate embodiments this prescription may be for a free form lens or for a commercially available lens having the closest lens power to the calculated custom lens power.

Also provided is a method for identifying a custom contact lens for a patient, including the steps of performing a bare eye examination on a patient to obtain at least a sphere power measurement for the patient's bare eye; selecting a fitting lens for said patient having a target sphere power or actual measured sphere power selected based on the sphere power measurement obtained from said bare eye examination; performing an over-refraction examination on the patient while the patient is wearing the selected fitting lens to obtain at least a measured sphere power; calculating a power delivered by the fitting lens on the patient's eye based on the results of the bare eye examination and over-refraction examination; calculating an Effectiveness Ratio using the calculated power delivered by the fitting lens and the target sphere power or actual sphere measurement of the selected fitting lens; and calculating a custom lens power for the patient using the Effectiveness Ratio and sphere measurement from the bare eye examination.

In one embodiment, the selected fitting lens has an actual measured sphere power and the Effectiveness Ratio is calculated based on the actual measured sphere power. In an alternative embodiment, the selected fitting lens has a target sphere power and the Effectiveness Ratio is calculated based on the target sphere power.

In further alternate embodiments, that the bare eye examination may be a subjective examination and may further be performed using a phoropter, or may be an objective examination and may further be performed using a refractometer or a device that measures the wavefront of the patient's eye. In yet another embodiment, the bare eye examination may be a combination subjective and objective examinations.

In yet another embodiment, the method further includes the step of prescribing a custom lens for said patient based on said calculated custom lens power, and the prescribed lens may further be a free form lens or a commercially available lens having the closest lens power to the calculated custom lens power.

The present invention also provides a computer system for identifying a custom contact lens for a patient including a memory, a processor, and an input device communicably coupled with said processor and memory and for receiving input from a user. The computer system is configured to receive as input from a user via the input device a target sphere power or actual measured sphere power of a selected fitting lens and results of a bare eye examination performed on the patient. The results include at least a sphere power measurement of the patient's eye and results of an over-refraction examination performed on the patient while wearing said fitting lens, with the results including at least a sphere power measurement. The processor is configured to calculate, based on the bare eye and over-refraction examinations, the power delivered by the fitting lens on the patient's eye, an Effectiveness Ratio, and a custom lens power for the patient based on the Effectiveness Ratio and sphere measurement from the bare eye examination. The computer system is further configured to provide as output the custom lens power and/or a custom contact lens prescription for the patient based on the custom lens power.

The lens prescribed may be a free form lens or a commercially available lens having the closest lens power to the calculated custom lens power.

Also provided is a method for identifying a custom contact lens for a patient, including the steps of receiving as input a target or actual measured sphere power of a patient's habitual lens; receiving as input results of an over-refraction examination of a patient wearing the habitual lens, wherein the results of the over-refraction examination include at least a measured sphere power; calculating the power delivered by the habitual lens on the patient's eye based on the input received for the habitual lens and from the over-refraction examination; calculating an Effectiveness Ratio using the calculated power delivered by the habitual lens and the target sphere power or actual measured sphere power of the habitual lens; and calculating a custom lens power for the patient using the Effectiveness Ratio and actual measured or target sphere power of the habitual lens.

In alternate embodiments, the actual measured sphere power of the habitual lens is received as input and the Effectiveness Ratio is calculated using the actual measured sphere power, or the target lens sphere power of the habitual lens is received as input and the Effectiveness Ratio is calculated using the target lens sphere power.

The method may further include the step of generating a custom contact lens prescription for the patient based on the calculated custom lens power, and the prescription may further be for a free form lens or a commercially available lens having the closest lens power to the calculated custom lens power.

These and other objects, features and advantages of the present invention will be apparent from the following detailed description of illustrative embodiments thereof, which is to be read in connection with the accompanying drawings.

DETAILED DESCRIPTION

Figure 1:
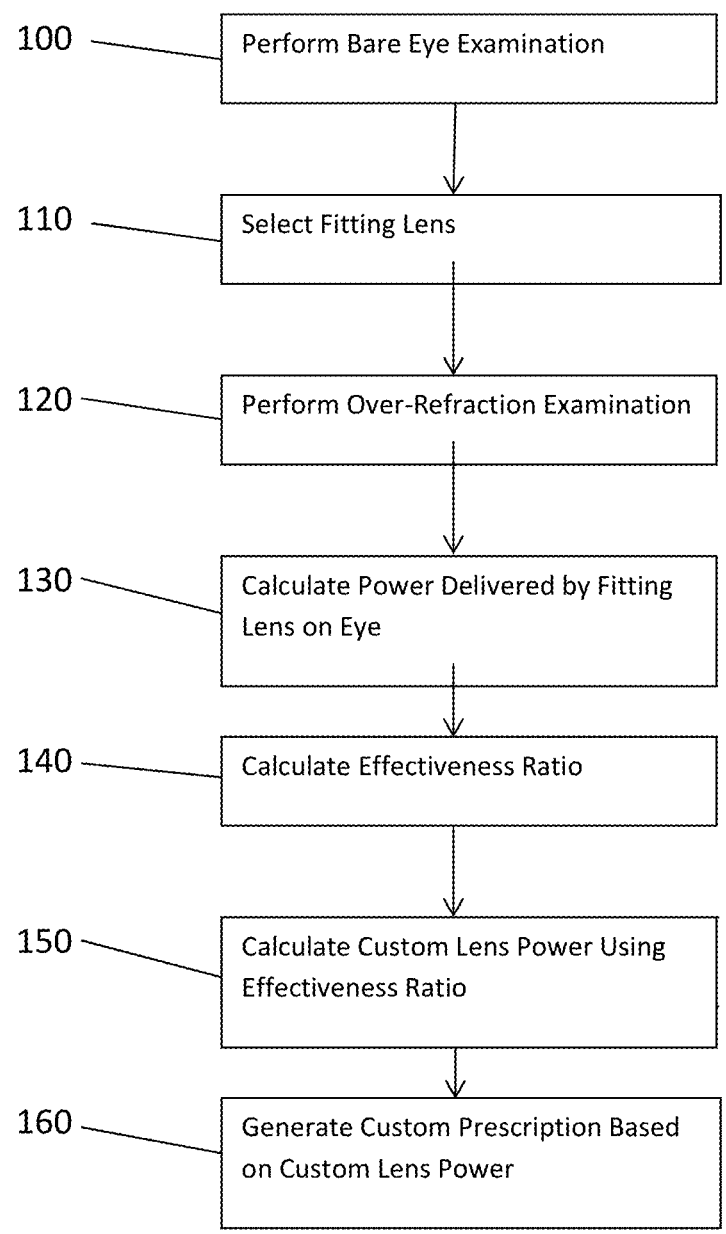
FIG. 1 is a flow chart illustrating steps of the present invention.

In one embodiment, the present system and method described herein leverages the ability to measure each contact lens that is produced in order to provide an improved means by which to design a customized sphere, astigmatic, multifocal or higher order aberration correcting contact lens. In an alternate, more basic embodiment, however, the present invention provides a means by which to generate a more precise prescription for a patient using any measurement system or trial or fitting lenses, now existing or introduced in the future. Several examples will be described in detail below, including examples using eyes with either single vision or astigmatic correction needs, fitting lenses that will be of type single vision (sphere power only) and astigmatic (sphere, cylinder and axis), and the cases where fitting lenses on different eyes initially either under-correct or over-correct the patient's vision needs.

For sake of comparison, an example of how a contact lens prescription is currently arrived (prior art) will be described first.

PRIOR ART EXAMPLE

First, a bare eye examination of the patient is performed using any traditional means as discussed above. For exemplary purposes, it is assumed that a bare eye examination is performed using a low resolution standard phoropter, yielding the following measurements:

| Sphere | Cylinder | Axis |
|---|---|---|
| −3.00 D | 0.00 D | 0° |

Based on this data a commercially available spherical powered contact lens having a labeled power (target power as opposed to actual measured power) of −3.00 D may be selected as a fitting lens and placed on the patient's eye. An over-refraction examination is then performed with the fitting lens on the eye, which reveals the following residuals:

| Sphere | Cylinder | Axis |
|---|---|---|
| 0.00 D | 0.00 D | 0° |

Based on this information, it is determined that the vision in this eye of the patient has been perfectly corrected. In this case, no further refraction or over-refraction examinations should be required and lenses for this eye can be ordered from the manufacturer/distributor, the order will be for −3.00 D single vision lenses. The fitting lens performed as expected.

However, as stated above, the low resolution phoropter will only provide eye data requirements to the nearest 0.25 D and therefore the eye may not be perfectly corrected but is deemed to be so within the measurement capability. It was also noted above that mass produced commercially available lenses may vary in lens power from target power by as much as ±0.25 D, and therefore there is no guarantee that the −3.00 D lenses ordered for this eye of the subject will perfectly correct the vision. In this case, given that only labeled lens power is known for each lens, including trial or fitting lenses, and that these lenses typically deviate from the targeted and labeled lens power, it is clear that the current method is inexact at best in providing a patient with an optimal lens and optimal vision correction.

Example 1

Fitting Lens UNDER Corrects Vision Need

According to the present invention and with reference also to FIG. 1, the eye care practitioner initially examines the patient's bare eye (step 100) in a manner similar to that described above which results in measured parameters of the patient's eye, including at least a measured sphere power. If a phoropter is used, however, it is preferable for it to be a high resolution phoropter able to measure in 0.125 diopter increments or smaller. For exemplary purposes, this first examination indicates the following bare eye measurements:

| Sphere | Cylinder | Axis |
|---|---|---|
| −2.875 D | 0.00 D | 0° |

Based on this data, a fitting lens is then selected (step 110) that preferably most closely corresponds to correct for the measured sphere power from the bare eye examination. As indicated previously, in contrast to lenses produced by traditional techniques, custom lenses produced by free form manufacturing can be readily measured for actual lens power of the final lens. As also indicated previously, each custom lens produced in this manner can readily be measured in the pre-hydrated state, and mathematically converted to a precise wet lens measurement by using known calibration parameters. As used herein, "actual measured sphere power" shall include either the actual measured, pre-hydrated sphere power or the wet sphere power mathematically calculated based on the actual measured, pre-hydrated sphere power. "Actual measured sphere power" shall also include the actual precise measured wet lens powers of any lenses used.

For purposes of illustration, we will assume that a fitting lens of exactly −3.07 D hydrated sphere power is available and will be placed on the subject's eye. This step provides critical increased accuracy in the process given that the actual lens power can be used to determine the desired custom lens, as opposed to labeled lens power. This level of accuracy was unattainable previously, and simply would not have otherwise been necessary given the large variation and inaccuracy of mass produced lenses that are commercially available. In accordance with what has been previously stated, however, and as will be more readily understood from what follows, is that accuracy of prescriptions may also be greatly improved even when trial or fitting lenses having a target labeled power are available to the ECP. For further sake of clarity, although the terms "trial" or "fitting" lens are used herein, it should be readily apparent that commercially salable lenses may be used, which will be deemed trial or fitting lenses herein for the sake of describing their use as temporary test or trial lenses for the patient for the over-refraction examination.

Once the trial or fitting lens is selected, a high resolution over-refraction examination is then performed (step 120) with the fitting lens on the eye, which reveals the following residuals:

| Sphere | Cylinder | Axis |
|---|---|---|
| −0.125 D | 0.00 D | 0° |

Based on this information, it is determined that the vision in this eye of the patient needs an additional −0.125 D of correction over and above the fitting lens powers. This provides the eye care practitioner with a critical piece of information that, prior to this system and method, was previously unavailable. In other words, by leveraging actual measured lens power instead of labeled lens power and high resolution exam data, one can obtain more precise information about how the lens actually behaves on the eye, and use this information to prepare a more precise prescription for a customized lens.

In this case the fitting lens did not perform as expected, since it did not fully correct the power need of the eye. Assuming that the eye does indeed need −2.875 D of correction, and from the free form manufacturing and metrology method knowing that the fitting lens was exactly a −3.07 D powered contact lens, the Power Delivered by the Fitting Lens on Eye is calculated (step 130) by:

Power Delivered by the Fitting Lens On Eye=Bare Eye Power Need minus FittingLens Overrefraction.

In this instance the

Power Delivered by the Fitting Lens On Eye=−2.875 D−−0.125 D=−2.75 D, meaning that the fitting lens on eye behaved like a −2.75 D lens.

We now introduce the term, "Effectiveness Ratio", which is entirely new to the present invention. The Effectiveness Ratio is defined as follows:

$$\text{Effectiveness Ratio} = \frac{\text{Power Delivered by the Fitting Lens On Eye }(D)}{In_{vitro}\text{ Measured or Target Labeled Fitting Lens Power }(D)}$$

where In vitro Measured Fitting Lens Power is defined as the actual measured power of the particular fitting lens used for over refraction. As will be described further below, it is preferably to use the actual measured fitting lens power, but the present invention will nevertheless provide increased accuracy even if only the target (labeled) lens power is available. As such, the Effectiveness Ratio is defined herein to include both, even though several examples below specifically utilize the actual, measured lens power.

The eye care practitioner observes the actual −3.07 D lens behaving like a −2.75 D lens when on the patient's eye and he/she can calculate the Effectiveness Ratio (step 140) by dividing the Power Delivered by the Fitting Lens on Eye by the actual, in-vitro measured lens power of the lens itself. Using the formula yields $$\text{Effectiveness Ratio} = \frac{-2.75(D)}{-3.07(D)} = 0.895765$$

It is seen that in this case, the Effectiveness Ratio of 0.895765 is less than 1.000 indicating that the fitting lens delivered less power correction to the eye than desired. As in earlier cases, this may be due to many reasons, including how the lens fits on the eye, patient accommodation, etc.

At this junction, the ECP could select another fitting lens, or proceed to use the Effectiveness Ratio to calculate an accurate custom lens target power for the patient (step 150). One method that can be used to calculate an accurate custom lens target power is by leveraging the Effectiveness Ratio via the following equation:

$$\frac{\text{In\_vitro Measured Fitting Lens Power }(D)}{\text{Power Delivered by the Fitting Lens On Eye }(D)} = \frac{\text{Custom Lens Power }(D)}{\text{Bare Eye Power Need }(D)}$$

Rewriting the equation gives:

$$\text{Custom Lens Power }(D) = \frac{(\text{Bare Eye Power Need}) \times (\text{In\_vitro Measured Fitting Lens Power})}{\text{Power Delivered by the Fitting Lens On Eye}}$$

Remembering that:

$$\text{Effectiveness Ratio} = \frac{\text{Power Delivered by the Fitting Lens On Eye }(D)}{\text{In\_vitro Measured Fitting Lens Power }(D)}$$

the inverse of the Effectiveness Ratio is defined as:

$$\frac{1}{\text{Effectiveness Ratio}} = \frac{\text{In\_vitro Measured Fitting Lens Power }(D)}{\text{Power Delivered by the Fitting Lens On Eye }(D)}$$

Substituting the Effectiveness Ratio formula into the Custom Lens Power formula yields the following equation:

$$\text{Custom Lens Power }(D) = \frac{\text{Bare Eye Power Need}}{\text{Effectiveness Ratio}}$$

Therefore, from this equation, the Custom Lens Power can be calculated that is needed to achieve the desired vision correction. For the example in this case, where the Bare Eye Power Need is −2.875 D, and the Effectiveness Ratio was calculated as 0.895765, the Custom Lens Power Requirement=−2.875/0.895765=−3.210 D The ECP can use this information to order the closest available commercially stocked lens, or to order custom free formed −3.210 D lenses for his/her patient, and assuming that the process by which the −3.07 D fitting lens was manufactured is used to fabricate the desired custom lens, and that the custom lens is manufactured to a very high standard, the custom lens should provide near optimal vision for the patient.

Data referenced in Example 1 is entered into the following table, for ease of reference.

| Example 1 Single Vision Need. Single Vision Fitting Lens UNDER Corrects | |
|---|---|
| A. Bare Eye Power Need (Sph, in diopters) | −2.875 |
| C. In-vitro Measured Fitting Lens Power (Sph, in diopters) | −3.070 |
| E. Over-Refraction using Fitting Lens (Sph, in diopters) | −0.125 |
| G. Sphere Power Delivered by the Fitting Lens on Eye (in diopters) G = A − E | −2.75 |
| H. Effectiveness Ratio. H = G/C | 0.895765 |
| K. Custom Lens Power Requirement (Sph, in diopters) K = A/H | −3.210 |
| L. Single Vision Lens ECP orders from stock (D) | −3.25 |

High resolution phoropters provide data to at least the nearest 0.125 D which is superior to the standard resolution method, but still the eye may not be perfectly corrected. Lenses (fitting or custom) produced via the free form process described in U.S. Pat. No. 8,317,505 are extremely precise, accurate and repeatable. Given the precise nature of the free form process, it has been determined that a standard deviation of actual measured lens power from the intended lens power of ±0.02 D can readily be achieved. Lenses fabricated via this technology are therefore ideal candidates for use in this invention. Best ECP practices, careful refractions and over-refractions, high resolution phoropters, precise lens manufacture and known lens powers are more likely to ensure success when using this invention. This invention may also be used however with low resolution refractions and over-refractions, lenses produced via any manufacturing technology, and labeled lens powers from commercially available lenses but the results may be suboptimal.

For further illustration of this principle, given the information above in Example 1 but using a low resolution phoropter instead of a high resolution one could have yielded a bare eye prescription of −3.00 D (instead of the higher resolution exam value of −2.875 D). If the precisely fabricated −3.07 D fitting lens was only labeled as −3.00 D and the low resolution over-refraction value of this lens on eye was −0.25 D, one could deduce that the targeted custom lens power would have been −3.25 D (−3.00 D-0.25 D). However, when utilizing the actual lens power of the fitted lens as opposed to simply the labeled lens power, and higher resolution refraction equipment, the eye care practitioner has information at his/her disposal that would result in a −3.210 D contact lens for the patient. He/she observes the actual behavior of a lens on the eye without the margin of error introduced by commonplace, but unknown deviations of commercially available lenses from their labeled power.

It is further noted that the examples described in detail herein include obtaining a sphere power from a bare eye examination. The present invention, however, can also be utilized to identify a more precise custom contact lens for a patient by initially using the patient's "habitual lens", or the lens that the patient currently uses as had been previously prescribed. In this instance, the bare eye examination is not performed, and the actual measured or target sphere power as labeled on the habitual lens is input rather than the sphere power as determined from the bare eye examination.

Example 2

Fitting Lens OVER Corrects Vision Need

Consider the case where the examination reveals the following bare eye measurements:

| Sphere | Cylinder | Axis |
|---|---|---|
| −2.875 D | 0.00 D | 0° |

For purposes of illustration, we will assume that a fitting lens of exactly −3.07 D hydrated power is available and will be placed on one of the subject's eyes. A high resolution over-refraction examination is then performed with the fitting lens on the eye, which reveals the following residuals:

| Sphere | Cylinder | Axis |
|---|---|---|
| +0.375 D | 0.00 D | 0° |

In this case the fitting lens did not perform as expected, since it did not fully correct the power need of the eye. Assuming that the eye does indeed need −2.875 D of correction, and from the free form manufacturing and metrology method knowing that the fitting lens was exactly a −3.07 D powered contact lens, the Power Delivered by the Fitting Lens On Eye=−2.875 D−+0.375 D=−3.25 D In other words, the fitting lens on eye behaved like a −3.25 D lens.

The eye care practitioner observes the actual −3.07 D lens behaving like a −3.25 D lens when on the patient's eye and he/she can establish the Effectiveness Ratio as:

$$\text{Effectiveness Ratio} = \frac{-3.25(D)}{-3.07(D)} = 1.058632$$

It is seen that in this case, the Effectiveness Ratio of 1.058632 is greater than 1.000 indicating that the fitting lens delivered greater power correction to the eye than desired.

Applying the method described above:

Custom Lens Power =

$$\frac{\text{Bare Eye Power Need }(D)}{\text{Effectiveness Ratio}} = \frac{-2.875}{1.058632} = -2.716D$$

The ECP can order custom free formed −2.716 D lenses for his/her patient, and assuming that the process by which the −3.07 D fitting lens was manufactured is used to fabricate the desired custom lens, and that the custom lens is manufactured to a very high standard, the custom lens should provide near optimal vision for the patient.

Data referenced in Example 2 is entered into the following table, for ease of reference.

| Example 2 Single Vision Need. Single Vision Fitting Lens OVER Corrects | |
|---|---|
| A. Bare Eye Power Need (Sph, in diopters) | −2.875 |
| C. In-vitro Measured Fitting Lens Power (Sph, in diopters) | −3.07 |
| E. Over-Refraction using Fitting Lens (Sph, in diopters) | 0.375 |
| G. Sphere Power Delivered by the Fitting Lens on Eye (in diopters) G = A − E | −3.25 |
| H. Effectiveness Ratio. H = G/C | 1.058632 |
| K. Custom Lens Power Requirement (Sph, in diopters) K = A/H | −2.716 |
| L. Single Vision Lens ECP orders from stock (D) | −2.75 |

Even though the cases described above have focused primarily on bare eye vision needs of just sphere power correction and single vision fitting lenses, this invention also applies to astigmatic vision needs, multifocal vision needs, higher order aberrated vision needs and diseased eye needs (for example Keratoconus), and can leverage single vision fitting lenses, astigmatic fitting lenses, multifocal fitting lenses or higher order aberration correcting fitting lenses.

For those skilled in the art, it should now be obvious that use of the Effectiveness Ratio in determining the correct power of lenses for patients can be utilized on any combination of vision need and fitting lens type and power(s). For example, the method can be used when the bare eye vision needs astigmatic correction but the fitting lens has only a single spherical power. Another example is that an astigmatic lens can be placed on an eye that just needs single vision correction, and the Effectiveness Ratio method also can be utilized. One further example is utilization of an astigmatic fitting lens on an astigmatic bare eye.

For example, astigmatic lenses have both a sphere power and cylindrical power component at a specified axis angle. Consider the typically labeled astigmatic lens of −3.00/−0.75×50°. The −3.00 D value refers to the sphere power along the 50° axis, and the −0.75 D value refers to the power that lies along a 140° axis (orthogonal to the sphere power axis) and is IN ADDITION TO the sphere power. Typically, the −3.00 D value is referred to as the "sphere power", and the −0.75 D value is referred to as the "cylinder power". Standard ophthalmic angular coordinate system convention is used here where 0° is at the 3 o'clock position, 90° is at the 12 o'clock position, 180° is at the 9 o'clock position and 270° is at the 6 o'clock position.

For the purpose of this patent, the "sphere power" may be referred to as the "Minor Power" and the "sum of the sphere power plus cylinder power" may be referred to as the "Major Power".

Minor Power(D)=sphere power(D)

Major Power(D)=sphere power(D)+cylinder power(D)

Another important formula used in astigmatic lenses is that of:

Equivalent Sphere Power(D)=sphere power(D)+½ cylinder power(D)

Using these formulae, the above example yields a Minor Power of −3.00 D, a Major Power of −3.75 D and an Equivalent Sphere Power of −3.375 D.

As stated, the Effectiveness Ratio method can be used on a multitude of different fitting lens types. In Examples 1-2 above, only single vision eye needs and single vision (sphere power only) fitting lenses were illustrated. Since these types of eyes and lenses are not usually labeled as having a cylinder power (since it equals 0.00 D), the cases above only had the value of the respective sphere powers propagating through the calculations, since in these examples:

sphere power=Minor Power=Major Power=Equivalent Sphere Power

Example 3

Astigmatic Eye, Single Vision Fitting Lens

Consider the case of an eye needing astigmatic correction and the use of a single vision fitting lens where the refraction examination reveals the following bare eye measurements:

| Sphere | Cylinder | Axis |
|---|---|---|
| −2.875 D | −0.875 D | 18° |

This refraction data can also be represented as:

Bare Eye Minor Power=−2.875 D

Bare Eye Major Power=−2.875+−0.875=−3.75 D

Bare Eye Equivalent Sphere Power=−2.875+½(−0.875)=−3.3125 D

Although not necessary for the Effectiveness Ratio method to be utilized, and any fitting lens power may be selected, one strategy is to choose a fitting lens that is as close to the equivalent sphere power of the bare eye power requirement as possible. For purposes of illustration, we will assume that a fitting lens of exactly −3.33 D hydrated power is available and will be placed on the subject's eye.

A high resolution over-refraction examination is then performed with the fitting lens on the eye, which reveals the following residuals:

| Sphere | Cylinder | Axis |
|---|---|---|
| +0.375 D | −0.625 D | 27° |

This over-refraction data can also be represented as:

Over-refraction Minor Power=+0.375 D

Over-refraction Major Power=+0.375+−0.625=−0.25 D

Over-refraction Equivalent Sphere Power=+0.375+½(−0.625)=+0.0625 D

In this case the fitting lens did not perform as expected, since it did not fully correct the power need of the eye. Assuming that the eye does indeed need −2.875/−0.875×18° of correction, and from the free form manufacturing and metrology method knowing that the fitting lens was exactly a −3.33 D single vision powered contact lens (with 0.00 D of cylinder power), there are several available methods to calculate the Effectiveness Ratio. These options are detailed below, and labeled as Example 3a, Example 3b and Example 3c.

Example 3a

Using the Bare Eye Minor Power as the Primary Basis for Calculating the Desired Custom Lens From the equations herein the Power Delivered by the Fitting Lens On Eye =
$$-2.875D - +0.375D = -3.25D$$

$$\text{Effectiveness Ratio} = \frac{-3.25(D)}{-3.33(D)} = 0.975976$$

Custom Lens Power =

$$\frac{\text{Bare Eye Power Need }(D)}{\text{Effectiveness Ratio}} = \frac{-2.875}{0.975976} = -2.946D$$

Remembering that there was a −0.625 D cylinder power component from the over-refraction exam, the ECP can order custom free formed −2.946/−0.625×27° lenses for his/her patient which should improve the patient's vision. Without using the Effectiveness Ratio, the ECP in this case may have elected to choose a −3.00/−0.75×30° stock lens for his/her patient, which does not leverage the high resolution refraction technique, nor free form manufacture of custom lenses.

Data referenced in Example 3a is entered into the following table, for ease of reference.

| Example 3a Astigmatic Need. Single Vision Fitting Lens. Calculations Primarily Based off MINOR power | | | |
|---|---|---|---|
| A. Bare Eye Power Need (Sph (D)/Cyl (D) × Axis (°)) | −2.875 | −0.875 | 18 |
| C. In-vitro Measured Fitting Lens Power (Sph, in diopters) | −3.33 | | |
| E. Over-Refraction using Fitting Lens (Sph (D)/Cyl (D) × Axis (°)) | 0.375 | −0.625 | 27 |
| G. Minor Power Delivered by the Fitting Lens on Eye (in diopters) G = A − E | −3.25 | | |
| H. Effectiveness Ratio. H = G/C | 0.975976 | | |
| K. Custom Lens Power Requirement (Sph (D)/Cyl (D) × Axis (°)) K{Sph} = A{Sph}/H K{Cyl} = E{Cyl} K{Axis} = E{Axis} | −2.946 | −0.625 | 27 |
| L. Astigmatic Lens ECP orders from stock (Sph (D)/Cyl (D) × Axis (°))) | −3.00 | −0.75 | 30 |

Example 3b

Using the Bare Eye Major Power as the Primary Basis for Calculating the Desired Custom Lens From the equations herein the Power Delivered by the Fitting Lens On Eye =
$$-3.75D - -0.25D = -3.50D$$

$$\text{Effectiveness Ratio} = \frac{-3.50(D)}{-3.33(D)} = 1.051051$$

Custom Lens Power =

$$\frac{\text{Bare Eye Power Need }(D)}{\text{Effectiveness Ratio}} = \frac{-3.75}{1.051051} = -3.568D$$

Remembering that this is the major power, which is the sum of the sphere power plus the cylinder power, that there was 0.00 D of cylinder correction in the fitting lens but that the cylinder component of the fitting lens over-refraction was −0.625 D, then the actual sphere power of the custom contact lens that the ECP could order would be:

sphere power(D)=Custom Lens Power(D)−cylinder power(D)

sphere power(D)=−3.568−−0.625=2.943 D cylinder power(D)=cylinder component of fitting lens over_refraction(D)

cylinder power=−0.625 D

The custom product that the ECP can order, having used these parameters in the Effectiveness Ratio calculations would be: −2.943/−0.625×27°, which should improve the patient's vision. Without using the Effectiveness Ratio, the ECP in this case may have elected to choose a −3.00/−0.75×30° stock lens for his/her patient, which does not leverage the high resolution refraction technique, or free forming of custom lenses. The axis value in this case is taken from the over-refraction data and not the bare eye data.

Data referenced in Example 3b is entered into the following table, for ease of reference.

Example 3b
Astigmatic Need. Single Vision Fitting Lens.
Calculations Primarily Based off MAJOR power

| | | | |
|---|---|---|---|
| A. Bare Eye Power Need (Sph (D)/Cyl (D) × Axis (°)) | −2.875 | −0.875 | 18 |
| C. In-vitro Measured Fitting Lens Power (Sph, in diopters) | −3.33 | | |
| E. Over-Refraction using Fitting Lens (Sph (D)/Cyl (D) × Axis (°)) | 0.375 | −0.625 | 27 |
| G. Major Power Delivered by the Fitting Lens on Eye (in diopters) G = (A{Sph} + A{Cyl}) − (E{Sph} + E{Cyl}) | −3.50 | | |
| H. Effectiveness Ratio. H = G/C | 1.051051 | | |
| K. Custom Lens Power Requirement (Sph (D)/Cyl (D) × Axis (°)) K{Cyl} = E{Cyl} K{Sph} = ((A{Sph} + A{Cyl})/H) − K{Cyl} K{Axis} = E{Axis} | −2.943 | −0.625 | 27 |
| L. Astigmatic Lens ECP orders from stock (Sph (D)/Cyl (D) × Axis (°))) | −3.00 | −0.75 | 30 |

Example 3c

Using the Bare Eye Equivalent Sphere Power Value as the Primary Basis for Calculating the Desired Custom Lens From the equations herein the Power Delivered by the Fitting Lens On Eye=Bare Eye Power Need minus FittingLens Overrefraction Power Delivered by the Fitting Lens On Eye=−3.3125−+0.0625 D=−3.375 D In this case, this is the Equivalent Sphere Power delivered by the lens to the eye.
The Effectiveness Ratio can be calculated as follows:

$$\text{Effectiveness Ratio} = \frac{-3.375(D)}{-3.33(D)} = 1.013514$$

Applying this Effectiveness Ratio of 1.013514 to calculate the true value of Equivalent Sphere Power correction that the bare eye needs, using the generic custom lens power equation herein of:

$$\text{Custom Lens Power }(D) = \frac{\text{Bare Eye Power Need }(D)}{\text{Effectiveness Ratio}}$$

leads to the Custom Lens Equivalent Sphere Power being:

$$\text{Custom Lens Equivalent Sphere Power} = \frac{-3.3125}{1.013514} = -3.268D$$

Remembering that there was 0.00 D of cylinder correction in the fitting lens and that the cylinder component of the fitting lens over-refraction was −0.625 D, then the Effectiveness Ratio also needs to be applied to the cylinder power component of the Bare Eye Need. Therefore:

$$\text{Custom Lens Power }(D) = \frac{\text{Bare Eye Power Need }(D)}{\text{Effectiveness Ratio}}$$

leading to the Custom Lens Cylinder Power component being:

$$\text{Custom Lens Cylinder Power component} = \frac{-0.625}{1.013514} = -0.617D$$

Since there was 0.00 D of cylinder power correction in the fitting lens, the axis of the custom lens to be ordered is taken from the axis of the fitting lens over-refraction exam, in this case 27°.

The final step in this method is to determine the minor power, or sphere power, of the custom lens to be designed and fabricated. The equation for Equivalent Sphere Power of:

Equivalent Sphere Power(D)=sphere power(D)+½ cylinder power(D)

can be re-arranged to give:

sphere power(D)=Equivalent Sphere Power(D)−½ cylinder power(D)

Substituting values from above into this equation yields:

sphere power=−3.268−−½(−0.617)=−2.960 D

The custom product that the ECP can order based off using the Effectiveness Ratio on the equivalent sphere power properties of the bare eye, fitting lens and over-refraction would be: −2.960/−0.617×27°, which should improve the patient's vision. Without using the Effectiveness Ratio, the ECP in this case may have elected to choose a −3.00/−0.75×30° stock lens for his/her patient, which does not leverage the high resolution refraction technique, nor free forming of custom lenses. The axis value in this case is taken from the over-refraction data and not the bare eye data.

Data referenced in Example 3c is entered into the following table, for ease of reference.

Example 3c
Astigmatic Need. Single Vision Fitting Lens.
Calculations Primarily Based off EQ Sph power

| | | | |
|---|---|---|---|
| A. Bare Eye Power Need (Sph (D)/Cyl (D) × Axis (°)) | −2.875 | −0.875 | 18 |
| C. In-vitro Measured Fitting Lens Power (Sph, in diopters) | −3.33 | | |
| E. Over-Refraction using Fitting Lens (Sph (D)/Cyl (D) × Axis (°)) | 0.375 | −0.625 | 27 |
| G. EQ Sph Power Delivered by the Fitting Lens on Eye (in diopters) G = (A{Sph} + (0.5 * A{Cyl})) − (E{Sph} + (0.5 * E{Cyl})) | −3.3750 | | |
| H. Effectiveness Ratio. H = G/C | 1.013514 | | |
| K. Custom Lens Power Requirement (Sph (D)/Cyl (D) × Axis (°)) K{Cyl} = E{Cyl}/H K{Sph} = ((A{Sph} + (0.5 * A{Cyl}))/ H) − (0.5 * K{Cyl}) K{Axis} = E{Axis} | −2.960 | −0.617 | 27 |
| L. Astigmatic Lens ECP orders from stock (Sph (D)/Cyl (D) × Axis (°))) | −3.00 | −0.75 | 30 |

Example 3a utilized the minor power as the focus for calculating the Effectiveness Ratio which was propagated through to other minor powers. Example 3b utilized the major power as the focus for calculating the Effectiveness Ratio which was propagated through to other major powers. Example 3c utilized the equivalent sphere power as the focus for calculating the Effectiveness Ratio which was propagated through to other equivalent sphere powers. It should be obvious now that any appropriate combination of minor power, major power or equivalent sphere power may be propagated through the entire calculation data set and used in combination with any other minor, major or equivalent sphere powers. For example, an Effectiveness Ratio calculated via a minor power can be applied to not only the minor power components, but also major power and equivalent sphere power components.

A different embodiment of this patent is the situation where an eye needs astigmatic correction, an astigmatic fitting lens is used for the over-refraction and the equivalent sphere power method is used, which is described further below as Example 4.

Example 4

Eye Needs Astigmatic Correction, an Astigmatic Fitting Lens is Used, and the Equivalent Sphere Power Method is Used to Calculate Effectiveness Ratio and Propagate to Custom Lens Design Parameters to be Generated Consider the same bare eye refraction examination from Example 3 that reveals the following refraction parameters:

| Sphere | Cylinder | Axis |
|---|---|---|
| −2.875 D | −0.875 D | 18° |

This refraction data can also be represented as:

Bare Eye Minor Power=−2.875 D

Bare Eye Major Power=−2.875+−0.875=−3.75 D

Bare Eye Equivalent Sphere Power=−2.875+½(−0.875)=−3.3125 D

For purposes of illustration, we will assume that a precisely manufactured and measured exact astigmatic fitting lens of −3.33/−0.14×23° is available and will be placed on the subject's eye.

A high resolution over-refraction examination is then performed with the fitting lens on the eye, which reveals the following residuals:

| Sphere | Cylinder | Axis |
|---|---|---|
| +0.375 D | −0.50 D | 33° |

This over-refraction data can also be represented as:

Over-refraction Minor Power=+0.375 D

Over-refraction Major Power=+0.375+−0.50=−0.125 D

Over-refraction Equivalent Sphere Power=+0.375+½(−0.50)=+0.125 D

In this case the fitting lens did not perform as expected, since it did not fully correct the power need of the eye. Assuming that the eye does indeed need −2.875/−0.875×18° of correction, and from the free form manufacturing and metrology method knowing that the fitting lens was exactly a −3.33/−0.14×23° hydrated astigmatic contact lens, one option the ECP has is to leverage the Effectiveness Ratio from using equivalent sphere values of the refraction, fitting lens and over-refraction exams.

To further improve the accuracy of the custom lens parameters that will be calculated, the rotation of the fitting lens on the eye needs to be known. This angular rotation position can be obtained from various sources and techniques, including but not limited to optical imaging devices such as slit lamps, wavefront devices, or any other commercially available device.

Assume that the astigmatic fitting lens on eye is measured as being rotated by 4° clockwise relative to the horizontal 0° to 180° line. Using equivalent sphere values throughout, from the equation:

Power Delivered by the Fitting Lens On Eye=Bare Eye Power Need minus FittingLens Overrefraction we get:

Power Delivered by the Fitting Lens On Eye=−3.3125−+0.125=−3.4375 D

Therefore the Equivalent Sphere Power delivered by the astigmatic fitting lens to the eye is −3.4375 D.

Using the equivalent sphere power components in the equation for Effectiveness Ratio of $$\text{Effectiveness Ratio} = \frac{\text{Power Delivered by the Fitting Lens On Eye }(D)}{\text{In\_vitro Measured Fitting Lens Power }(D)}$$

yields an Effectiveness Ratio of:

$$\text{Effectiveness Ratio} = \frac{-3.4375}{-3.33 + \frac{1}{2}(-0.14)} = -\frac{-3.4375}{-3.4} = 1.011029$$

Applying this Effectiveness Ratio of 1.011029 to calculate the true value of Equivalent Sphere Power correction that the bare eye needs, using the generic custom lens power equation of:

$$\text{Custom Lens Power } (D) = \frac{\text{Bare Eye Power Need } (D)}{\text{Effectiveness Ratio}}$$

leads to the Custom Lens Equivalent Sphere Power being:

$$\text{Custom Lens Equivalent Sphere Power} = \frac{-3.3125}{1.011029} = -3.276D$$

Remembering that there is −0.14 D of cylinder correction in the astigmatic fitting lens, that the sphere power of the fitting lens is at an angle of 23° and that the position of the fitting lens on eye is 4 degrees clockwise from the 0° to 180° horizontal line, an additional step using a standard business practice of calculating cross-cylinders needs to be performed.

Cross-cylinder calculations are fairly simple, and are based on vector resolution of the power components in orthogonal space. There are many different cross-cylinder calculators freely available on the internet. Basically, the inputs to the calculations are the sphere power components, cylinder power components and axis components of the bare eye refraction exam, the lens placed on the eye, the resulting parameters from the over-refraction exam, the rotation of the lens on the eye, and a vertex distance. Vertex distance is the distance between the back surface of a corrective lens and the front of the cornea, and is typically in the range of 10-15 mm. The cross-cylinder calculations basically enable differently oriented sphere power and cylinder power profiles to be combined and results in a recommended corrective astigmatic prescription.

Cross-cylinder calculations are needed in this embodiment example (example 4) since the bare eye sphere power axis, the fitting lens sphere power axis and the over-refraction sphere power axis are all different (18°, 23° and 33° respectively)

Using the following inputs:

| | |
|---|---|
| Bare eye parameters (sph/cyl × axis) of | −2.875/−0.875 × 18° |
| Fitting lens powers (sph/cyl × axis) of | −3.330/−0.140 × 23° |
| Over-refraction parameters (sph/cyl × axis) of | +0.375/−0.500 × 33° |
| Fitting lens rotation on eye of | +4° Clockwise |
| Vertex distance of | 15.00 mm | yields a recommended prescription of −2.961/−0.627×34°, partially based on the label powers of the fitting lens.

Cross-cylinder calculations rely on the fact that power correction applied to the eye by the fitting lens is equal to the labeled powers of the lens being fitted. Throughout this patent, it has been shown that even lenses made and measured to high precision tolerances do not necessarily impart the true value of the measured lens powers to the eye, resulting in either over- or under-correction.

Taking this example and remembering that the exact in-vitro measured fitting lens parameters are −3.330/−0.140×23°, we get:

the in-vitro fitting lens minor power=−3.330 D, and the in-vitro fitting lens cylinder power=−0.140 D.

The power delivered by the fitting lens on eye can be calculated by multiplying the in-vitro measured values by the Effectiveness Ratio. Therefore the minor power delivered by the fitting lens=−3.330×1.011029=−3.367 D, and the cylinder power delivered by the fitting lens=−0.140×1.011029=−0.142 D.

Of course the physical axis of the lens does not change from what is measured in-vitro to when it is placed on the eye, but there may be a different over-refraction angle based on how the lens fits.

Using the sphere power and cylinder power delivered to the eye by the fitting lens of −3.367/−0.142×23° in the cross-cylinder calculator as an input, the cross-cylinder calculation inputs are:

| | |
|---|---|
| Bare Eye parameters (sph/cyl × axis) | −2.875/−0.875 × 18° |
| Actual Powers imparted by Fitting Lens (sph/cyl × axis) | −3.367/−0.142 × 23° |
| Over-refraction parameters (sph/cyl × axis) | +0.375/−0.500 × 33° |
| Fitting Lens rotation on Eye | +4° Clockwise |
| Vertex Distance | 15.00 mm | and the output yields a recommended prescription of −2.998/−0.629×34°, partially based on the actual on eye performance of the astigmatic fitting lens.

If custom lenses were designed and manufactured to these −2.998/−0.629×34 parameters and placed on the eye as in this illustration, the lens would over correct based on the Effectiveness Ratio of 1.011029. The final step therefore is to convert these parameters into a new custom prescription by dividing each of the power components by the Effectiveness Ratio using the following equation:

$$\text{Custom Lens Power } (D) = \frac{\text{Bare Eye Power Need } (D)}{\text{Effectiveness Ratio}}$$

This leads to a final custom prescription for example 4 being:

$$\text{Custom Sphere Power} = \frac{-2.998}{1.011029} = -2.965D$$

$$\text{Custom Cylinder Power} = \frac{-0.629}{1.011029} = -0.622D$$

Custom Axis = 34°

The custom product that the ECP can order, having used these parameters in the Effectiveness Ratio calculations would be: −2.965/−0.622×34°, which should improve the patient's vision. Without using the Effectiveness Ratio, the ECP in this case may have elected to choose a −3.00/−0.75×30° stock lens for his/her patient, which does not leverage the high resolution refraction technique, nor free forming of custom lenses.

Data referenced in Example 4 is entered into the following table, for ease of reference.

Example 4
Astigmatic Need. Astigmatic Fitting Lens.
Calculations Primarily Based off EQ Sph power

| | | | | |
|---|---|---|---|---|
| A. Bare Eye Power Need (Sph (D)/Cyl (D) × Axis (°)) | −2.875 | −0.875 | 18 | |
| C. In-vitro Measured Fitting Lens Power (Sph, in diopters) | −3.33 | −0.14 | 23 | |
| E. Over-Refraction using Fitting Lens (Sph (D)/Cyl (D) × Axis (°)) | 0.375 | −0.500 | 33 | |
| G. EQ Sph Power Delivered by the Fitting Lens on Eye (in diopters) G = (A{Sph} + (0.5 * A{Cyl})) − (E{Sph} + (0.5 * E{Cyl})) | −3.4375 | | | |
| H. Effectiveness Ratio H = G/(C{Sph} + (0.5 * C{Cyl})) | 1.011029 | | | |
| I. Actual Powers Delivered to Eye (Sph (D)/Cyl (D) × Axis (°)) I{Sph} = C{Sph} * H I{Cyl} = C{Cyl} * H I{Axis} = C{Axis} | −3.367 | −0.142 | 23 | |
| J. Cross-cylinder Output (Sph (D)/Cyl (D) × Axis (°)) | −2.998 | −0.629 | 34 | |
| K. Custom Lens Power Requirement (Sph (D)/Cyl (D) × Axis (°)) K{Sph} = I{Sph}/H{Sph} K{Cyl} = I{Cyl}/H{Cyl} K{Axis} = J{Axis} | −2.965 | −0.622 | 34 | |
| L. Astigmatic Lens ECP orders from stock (Sph (D)/Cyl (D) × Axis (°)) | −3.00 | −0.75 | 30 | |

Figure 2:
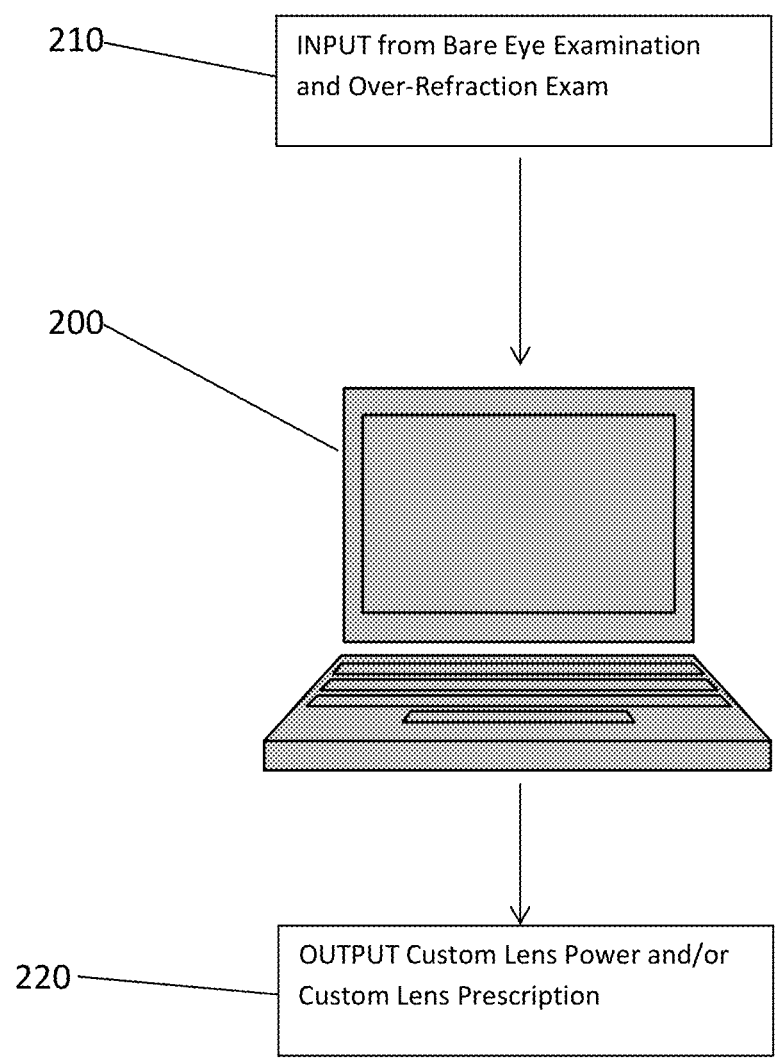
FIG. 2 illustrates the use of a computer system in conjunction with the present invention.

It should be readily understood by those skilled in the art that the measurements and calculations described above can be performed with the assistance of a computer and associated software. As shown in FIG. 2, the computer and associated software 200 may receive as input 210 results of the bare eye examination and over-refraction examination as described above, and subsequently perform the calculations relating to the power delivered by the fitting lens on the eye and the Effectiveness Ratio, and thus generate as output 210 the custom lens power for that patient and/or a custom lens prescription based on the custom lens power. The computer and related software may reside at the location of the ECP, or may be remote. Further, the generated custom lens power may be transmitted directly to the manufacturer, particularly in the event that a free form custom lens is desired, or the data may be transmitted to the manufacturer and the custom lens power generated on site at the manufacturer.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A method for identifying a custom contact lens for a patient, comprising:
   receiving as input results from a bare eye examination of a patient including at least a measured sphere power;
   receiving as input a target or actual measured sphere power of a fitting lens selected based on said measured sphere power;
   receiving as input results of an over-refraction examination of a patient wearing said fitting lens, wherein the results of the over-refraction examination include at least a measured sphere power;
   calculating the power delivered by the fitting lens on the patient's eye based on input received from the bare eye examination and over-refraction examinations;
   calculating an effectiveness ratio using the calculated power delivered by the fitting lens and the target or actual measured sphere power of the fitting lens; and
   calculating a custom lens power for said patient using the effectiveness ratio and measured sphere power from the bare eye examination.

2. The method according to claim 1, wherein the actual measured sphere power of the fitting lens is received as input, and wherein the effectiveness ratio is calculated using the actual measured sphere power.

3. The method according to claim 1, wherein the target lens power of the fitting lens is received as input, and wherein the effectiveness ratio is calculated using the target lens power.

4. The method according to claim 1, wherein the bare eye examination is a subjective examination.

5. The method according to claim 4, wherein the subjective examination is performed using a phoropter.

6. The method according to claim 5, wherein the phoropter has a resolution of at least 0.25 D.

7. The method according to claim 5, wherein the phoropter has a resolution of at least 0.125 D.

8. The method according to claim 1, wherein the bare eye examination is an objective examination.

9. The method according to claim 8, wherein the objective examination is performed using a refractometer.

10. The method according to claim 8, wherein the objective examination is performed using a device that measures the wavefront of the patient's eye.

11. The method according to claim 1, wherein the bare eye examination is a combination subjective and objective examination.

12. The method according to claim 1, further comprising the step of generating a custom contact lens prescription for said patient based on the calculated custom lens power.

13. The method according to claim 12, wherein the prescription is for a free form lens.

14. The method according to claim 12, wherein the prescription is for a commercially available lens having the closest lens power to the calculated custom lens power.

15. A method for identifying a custom contact lens for a patient, comprising:
   performing a bare eye examination on a patient to obtain at least a sphere power measurement for said patient's bare eye;
   selecting a fitting lens for said patient having a target or actual measured sphere power measurement selected based on the sphere measurement obtained from said bare eye examination;
   performing an over-refraction examination on said patient while said patient is wearing said selected fitting lens to obtain at least a measured sphere power;
   calculating a power delivered by the fitting lens on the patient's eye based on the results of the bare eye examination and over-refraction examination;
   calculating an effectiveness ratio using the calculated power delivered by the fitting lens and the target or actual sphere measurement of the selected fitting lens; and
   calculating a custom lens power for said patient using said effectiveness ratio and sphere measurement from the bare eye examination.

16. The method according to claim 15, wherein the selected fitting lens has an actual measured sphere power, and wherein the effectiveness ratio is calculated based on the actual measured sphere power.

17. The method according to claim 15, wherein the selected fitting lens has a target sphere power, and wherein the effectiveness ratio is calculated based on the measured sphere power.

18. The method according to claim 15, wherein the bare eye examination is a subjective examination.

19. The method according to claim 18, wherein the subjective examination is performed using a phoropter.

20. The method according to claim 19, wherein the phoropter has a resolution of at least 0.25 D.

21. The method according to claim 19, wherein the phoropter has a resolution of at least 0.125 D.

22. The method according to claim 15, wherein the bare eye examination is an objective examination.

23. The method according to claim 22, wherein the objective examination is performed using a refractometer.

24. The method according to claim 22, wherein the objective examination is performed using a device that measures the wavefront of the patient's eye.

25. The method according to claim 15, wherein the bare eye examination is a combination subjective and objective examination.

26. The method according to claim 15, further comprising the step of prescribing a custom lens for said patient based on said calculated custom lens power.

27. The method according to claim 26, wherein the prescribed lens is a free form lens.

28. The method according to claim 26, wherein the prescribed lens is a commercially available lens having the closest lens power to the calculated custom lens power.

29. A method for identifying a custom contact lens for a patient, comprising:

receiving as input a target or actual measured sphere power of a patient's habitual lens;

receiving as input results of an over-refraction examination of a patient wearing said habitual lens, wherein the results of the over-refraction examination include at least a measured sphere power;

calculating the power delivered by the habitual lens on the patient's eye based on the input received for the habitual lens and from the over-refraction examination;

calculating an effectiveness ratio using the calculated power delivered by the habitual lens and the target or actual measured sphere power of the habitual lens; and calculating a custom lens power for said patient using the effectiveness ratio and actual measured or target sphere power of the habitual lens.

30. The method according to claim 29, wherein the actual measured sphere power of the habitual lens is received as input, and wherein the effectiveness ratio is calculated using the actual measured sphere power.

31. The method according to claim 29, wherein the target lens power of the habitual lens is received as input, and wherein the effectiveness ratio is calculated using the target lens power.

32. The method according to claim 29, further comprising the step of generating a custom contact lens prescription for said patient based on the calculated custom lens power.

33. The method according to claim 32, wherein the prescription is for a free form lens.

34. The method according to claim 32, wherein the prescription is for a commercially available lens having the closest lens power to the calculated custom lens power.

* * * * *